United States Patent
Barresi et al.

(10) Patent No.: US 6,610,672 B2
(45) Date of Patent: Aug. 26, 2003

(54) COMPOSITIONS INCLUDING REDUCED MALTO-OLIGOSACCHARIDE PRESERVING AGENTS, AND METHODS FOR PRESERVING A MATERIAL

(75) Inventors: Frank W. Barresi, Coralville, IA (US); Richard L. Antrim, Solon, IA (US)

(73) Assignee: Grain Processing Corporation, Mucatine, IA (US)

(*) Notice: Subject to any disclaimer, the term of this patent is extended or adjusted under 35 U.S.C. 154(b) by 86 days.

(21) Appl. No.: 10/043,365

(22) Filed: Jan. 9, 2002

(65) Prior Publication Data

US 2002/0115637 A1 Aug. 22, 2002

Related U.S. Application Data

(62) Division of application No. 09/693,496, filed on Oct. 20, 2000.
(60) Provisional application No. 60/160,611, filed on Oct. 20, 1999, and provisional application No. 60/160,615, filed on Oct. 20, 1999.

(51) Int. Cl.$^7$ .................. A61K 31/715; A01N 1/00; A01N 1/02
(52) U.S. Cl. .................. 514/58; 514/54; 514/25; 536/45; 536/55.3; 536/102; 536/104; 536/105; 424/195.1; 426/548; 435/2; 435/1.1
(58) Field of Search ............... 514/54, 58, 25; 536/45, 55.3, 102, 104, 105; 424/195.1; 426/548; 435/2, 1.1

(56) References Cited

U.S. PATENT DOCUMENTS

| | | |
|---|---|---|
| 2,280,975 A | 4/1942 | Power |
| 3,219,656 A | 11/1965 | Boettner |
| 3,639,389 A | 2/1972 | Hull |
| 3,876,794 A | 4/1975 | Rennhard |
| 3,890,300 A | 6/1975 | Huchette et al. |

(List continued on next page.)

FOREIGN PATENT DOCUMENTS

| | | |
|---|---|---|
| DE | 19/751630 A1 | 5/1999 |
| EP | 0 142 725 A1 | 5/1985 |
| EP | 0 142 725 A1 | 8/1987 |
| EP | 0 548 399 B1 | 6/1993 |
| EP | 0 577 519 B1 | 1/1994 |

(List continued on next page.)

OTHER PUBLICATIONS

Arts et al., "Hydrogen Peroxide and Oxygen in Catalytic Oxidation of Carbohydrates and Related Compounds" *Synthesis*, 597–613 (*Jun. 1997*).
Bell et al., "Glass Transition Explanation for the Effect of Polyhydroxy Compounds on Protein Denaturation in Dehydrated Solids," *Journal of Food Science*, 61 (2), 372–374 (*1996*).

(List continued on next page.)

*Primary Examiner*—James O. Wilson
*Assistant Examiner*—Devesh Khare
(74) *Attorney, Agent, or Firm*—Leydig, Voit & Mayer, LTD

(57) ABSTRACT

Disclosed is a composition that includes a material that is susceptible to degradation and a preserving agent in an amount effective to preserve the material comprising one or more reduced malto-oligosaccharide species. The preserving agent can include a single reduced malto-oligosaccharide species or a plurality of such species. Further disclosed is a method of preserving a material. The method generally includes contacting the material with a preserving agent containing a preserving effective amount of one or more reduced malto-oligosaccharide species. Solutions, powders, glasses, gels, and the like containing the chemically reactive material(s) and a preserving effective amount of one or more reduced malto-oligosaccharide species may be prepared.

8 Claims, 1 Drawing Sheet

U.S. PATENT DOCUMENTS

| | | |
|---|---|---|
| 3,928,318 A | 12/1975 | Panusch et al. |
| 3,935,284 A | 1/1976 | Kruse |
| 3,963,788 A | 6/1976 | Kruse et al. |
| 4,154,744 A | 5/1979 | Hammada et al. |
| 4,223,129 A | 9/1980 | Roth et al. |
| 4,248,895 A | 2/1981 | Stroz et al. |
| 4,248,945 A | 2/1981 | Alvarez et al. |
| 4,279,931 A | 7/1981 | Verwaerde et al. |
| 4,322,569 A | 3/1982 | Chao et al. |
| 4,336,152 A | 6/1982 | Like et al. |
| 4,346,116 A | 8/1982 | Verwaerde et al. |
| 4,445,938 A | 5/1984 | Verwaerde et al. |
| 4,463,116 A | 7/1984 | Koyama et al. |
| 4,675,293 A | 6/1987 | Gibs |
| 4,680,180 A | 7/1987 | Bussiere et al. |
| 4,717,765 A | 1/1988 | Hirao et al. |
| 4,728,510 A | 3/1988 | Shibanai et al. |
| 4,797,478 A | 1/1989 | Lebuhn et al. |
| 4,845,208 A | 7/1989 | Fuertes et al. |
| 4,985,553 A | 1/1991 | Fuertes et al. |
| 4,996,306 A | 2/1991 | McDaniel, Jr. et al. |
| 5,034,231 A | 7/1991 | Yatka et al. |
| 5,098,893 A | 3/1992 | Franks et al. |
| 5,109,128 A | 4/1992 | Schumacher et al. |
| 5,171,600 A | 12/1992 | Young et al. |
| 5,188,859 A | 2/1993 | Lodge et al. |
| 5,290,765 A | 3/1994 | Wettlaufer et al. |
| 5,334,287 A | 8/1994 | Hartmann et al. |
| 5,348,737 A | 9/1994 | Syed et al. |
| 5,354,424 A | 10/1994 | Rha et al. |
| 5,464,642 A | 11/1995 | Villagran et al. |
| 5,464,643 A | 11/1995 | Lodge |
| 5,478,593 A | 12/1995 | Serpelloni et al. |
| 5,493,014 A | 2/1996 | Caboche |
| 5,506,353 A | 4/1996 | Subramaniam |
| 5,520,840 A | 5/1996 | Massaro et al. |
| 5,523,108 A | 6/1996 | Wansor et al. |
| 5,571,547 A | 11/1996 | Serpeilloni et al. |
| 5,601,863 A | 2/1997 | Borden et al. |
| 5,620,873 A | 4/1997 | Ohkuma et al. |
| 5,627,273 A | 5/1997 | Thomaides et al. |
| 5,629,042 A | 5/1997 | Serpelloni et al. |
| 5,641,477 A | 6/1997 | Syed et al. |
| 5,655,552 A | 8/1997 | Samain |
| 5,656,584 A | 8/1997 | Angell et al. |
| 5,690,956 A | 11/1997 | Lau et al. |
| 5,715,849 A | 2/1998 | Vanbraekel |
| 5,720,978 A | 2/1998 | Morehouse |
| 5,756,438 A | 5/1998 | Rau et al. |
| 5,772,013 A | 6/1998 | Kunz et al. |
| 5,780,620 A | 7/1998 | Mandai et al. |
| 5,795,852 A | 8/1998 | He et al. |
| 5,851,300 A | 12/1998 | Linhart et al. |
| 5,853,487 A | 12/1998 | Tang et al. |
| 5,866,533 A | 2/1999 | Beck et al. |
| 5,900,261 A | 5/1999 | Ribadeau-Dumas et al. |
| 5,922,386 A | 7/1999 | Reed et al. |
| 5,925,396 A | 7/1999 | Reed et al. |
| 5,928,700 A | 7/1999 | Zimmerman et al. |
| 5,936,081 A | 8/1999 | Degelmann et al. |
| 5,955,448 A | 9/1999 | Colaco et al. |
| 5,965,501 A | 10/1999 | Rattinger et al. |
| 6,056,980 A | 5/2000 | Unno et al. |
| 6,107,348 A | 8/2000 | Nakano et al. |
| 6,242,224 B1 | 6/2001 | Nakano et al. |

FOREIGN PATENT DOCUMENTS

| | | |
|---|---|---|
| EP | 0 670 368 A2 | 9/1995 |
| EP | 0 618 286 A1 | 10/1995 |
| EP | 0 577 519 B1 | 4/1996 |
| EP | 0 775 709 A1 | 5/1997 |
| EP | 0 791 658 A1 | 8/1997 |
| EP | 0 839 916 A1 | 5/1998 |
| EP | 0 854 149 A1 | 7/1998 |
| GB | 526839 | 9/1940 |
| JP | 4-148661 A | 5/1992 |
| JP | 05103586 A | 4/1993 |
| JP | 05294837 A | 11/1993 |
| JP | 10-028531 | 2/1998 |
| WO | WO 92/14761 A1 | 9/1992 |
| WO | WO 92/18542 A1 | 10/1992 |
| WO | WO 95/07303 A1 | 3/1995 |
| WO | WO 95/18157 A1 | 7/1995 |
| WO | WO 96/10586 | 4/1996 |
| WO | WO 96/11589 A1 | 4/1996 |
| WO | WO 97/29133 A1 | 8/1997 |
| WO | WO 97/34861 A1 | 9/1997 |
| WO | WO 98/24972 A1 | 6/1998 |
| WO | WO 98/42814 A1 | 10/1998 |
| WO | WO 98/42818 A1 | 10/1998 |
| WO | WO 98/56827 | 12/1998 |
| WO | WO 99/11748 A1 | 3/1999 |
| WO | WO 99/36442 | 7/1999 |
| WO | WO 99/36442 A1 | 7/1999 |
| WO | WO 00/32157 A1 | 6/2000 |
| WO | WO 01//14394 A2 | 3/2001 |

OTHER PUBLICATIONS

Bender, "Studies of the Inhibition by Malto–Oligosaccharides of the Cycliation Reaction Catalyzed by the Cyclodextrin Glycosyltransferase from Klebsiella Pneumoniae M5 al with Glycogen," *Carbohydrate Research*, 135 (2), 291–302 (*Abstract*) (*1985*).

Bendiak, "Nuclear Magnetic Resonance Spectroscopy of Peracetylated Oligosaccharides having C–labeled carbonyl Groups in lieu of permethylation Analysis for Establishing Linkage Substitutions of Sugars," *Carbohydrate Research*, 315, 206–221 (*1999*).

Glattfeld et al, "The caralytic Dehydrogenation of Sugar Alcohols," *Journal of the American Chemical Society*, 60 (9), 2013–2023 (*1938*).

Kusano et al, Effects of Reduced Malto–Oligosaccharides on the Thermal Stability of Pullulansae from Bacillus Acidopullulyticus, *Carbohydrate Research*, 199 (1) 83–89 (*1990*).

*Handbook of Analytical Derivatization Reactions*, John Wiley & Sons, Inc., New York, New York, 528–584 (1979).

Kearsley et al., "Production and Physiochemical Properties of Hydrogenated Glucose Syrups," *Die Starke*, 29 (12) 425–429 (1977).

Kearsley et al., "The Production and Properties of Glucose Syrups, III. Sweetness of Flucose Syrups and Related Carbohydrates," *Starch/Starke* 32, 244–247 (1980).

Leroy, "Hydrogenated Starch Hydrolysates," *Health and Sugar Substitutes*, Proc. ERGOB Conference, Geneva, 114–119 (1978).

McNeil, "Elimination of Internal Glycosyl Residues During Chemical Ionization–Mass Spectrometry of Per–O–Alkylated Oligosaccharide–Alditols," *Carbohydrate Research*, 123, 31–40 (*1983*).

Nakgawa et al. "Construction from a Single Parent of Baker's Yeast Strains with High Freeze Tolerance and Fermentative Activity in Both Lean and Sweet Doughs," Tokyo Research Laboratories, *App. Environ. Microbiol.*, 60(*1*), 3499–3502 (*1994*).

O'Brien, "Stability of Trehalose, Sucrose and Glucose to Nonenzymatic Browning in Model Systems," *Journal of Food Science, 61(4), 679–682 (1996)*.

Rodriguez de Sotillo et al., "Potato Peel Waste: Stability and Antioxidant Activity of a Freeze–Dried Extraact," *Journal of Food Science, 59 (5), 1031–1033 (1994)*.

Roper, "Selective Oxidation of D–Glucose: Chiral Intermediates for Industrial Utilization," Carbohydrates as Organic Raw Materials, 268–288 (1991).

Rossi et al., "Stabilization of the Restriction Enzyme Eco RI Dried with Trehalose and Other Selected Glass–Forming Solutes," *Biotechnol. Prog., 13(5), 609–616 (1997)*.

Schebor et al., "Glassy State and Thermal Inactivation of Invertase and Lactase in Dried Amorphous Matrices," *Biotechnology Process, 13 (6), 857–863 (Abstract) (1997)*.

Heyns et al., "Die Darstellung der L–Gulose," Katalytische Oxydationen, 91 (13) 1720–1724 (1958).

Heyns et al., "Selektive Katalytische Oxydationen mit Edelmetall–Katalysatoren," *Angewandte Chem. 69 (13–14), 600–608 (Jul.15, 1957)*.

Eskuchen, R. et al., "Technology and Production of Alkyl Polyglycosides," in Hill et al., ed. Alky *Polyglycosides: Technology, Properties and Applications*, VCH Publishers Inc., N.Y., N.Y. 1997.

Search Report EP 01 30 5247 (Nov. 13, 2001).

Reference Summary to Yalpani, "Supercritical Fluids: Puissant Medica for the Modification of Polymers and Biopolymers" Polymer, vol. 34 (1993), pp. 1102–1105.

US 6,610,672 B2

COMPOSITIONS INCLUDING REDUCED MALTO-OLIGOSACCHARIDE PRESERVING AGENTS, AND METHODS FOR PRESERVING A MATERIAL

CROSS-REFERENCE TO RELATED APPLICATIONS

This application is a divisional of allowed U.S. patent application Ser. No. 09/693,496, filed Oct. 20, 2000, which claims the benefit of prior provisional application No. 60/160,611, filed Oct. 20, 1999, and prior provisional application No. 60/160,615, filed Oct. 20, 1999.

TECHNICAL FIELD OF THE INVENTION

The present invention relates to the preservation of materials that are susceptible to degradation and methods for inhibiting the degradation of such materials.

BACKGROUND OF THE INVENTION

Certain materials are sufficiently stable that they can be isolated, purified, and stored at room temperature. However, there are certain materials (e.g., chemically reactive and/or bioactive materials) that are not sufficiently stable to be stored long term without utilizing a more elaborate stabilization and/or storage procedure. For some materials, degradation can occur in terms of structural change and/or loss of activity or function as a result of isolation or upon storage. Such degradation often occurs in two settings: under the stresses of processing or isolating the material (e.g., mixing, heating, extracting, pumping, drying, freezing, distilling, extruding or the like), and under storage conditions (i.e., after isolation). For example, during drying or freezing processes, denaturation of proteins and destruction of liposome structure can occur. Upon storage (after drying or freezing), oxidation and free radical attack also can promote degradation of bioactive materials.

In some instances, it is desirable to stabilize and/or store certain materials in the presence of a preserving agent (i.e., a protective agent). It is advantageous to employ a preserving agent that has the ability to stabilize such materials under both isolation and storage conditions. In this respect, the preserving agent should have the ability to protect the material from degradation or loss of function under the stresses of isolation and also during storage.

Certain carbohydrates have been used as preserving agents for various bioactive materials (e.g., enzymes, tissues, organelles, and the like). The incorporation of certain bioactive materials in glassy or rubbery carbohydrate compositions is said to be an effective approach in stabilizing various chemically reactive materials, for example, as purportedly described in U.S. Pat. No. 5,098,893. The ability of carbohydrate compositions in the glassy state to stabilize bioactive materials also may be related to the glass transition temperature of the composition (see, e.g., Bell et al. *Journal of Food Science*, 61, 372–374 (1996)). Certain non-reducing sugars have been used as preserving agents in the stabilization of bioactive materials with varying degrees of success. For example, U.S. Pat. No. 5,290,765 purports to describe the use of sucrose in the protection of lysozyme enzyme from the stresses of air-drying, and also from the destructive reactions that can occur upon storage. Rossi et al., *Biotechnol. Prog.*, 13, 609–618 (1997) purports to describe the use of trehalose and sucrose in the stabilization of enzyme EcoRI.

While certain sugars such as sucrose and trehalose are often deemed advantageous in connection with protection of certain materials, these sugars are deficient in certain respects. For example, sucrose is generally considered quite labile, and can convert to fructose and glucose. Trehalose has good preserving properties for certain bioactive materials, but the high cost of trehalose can limit its use as a preserving agent. Moreover, reduced (i.e. hydrogenated) sugars such as sorbitol or other low molecular weight hydrogenated starch hydrolysates, or other low molecular weight compounds lack certain functional properties relating, for example, to water binding, molecular weight, osmolality, viscosity, and the like and are thus unsuitable for use in connection with certain applications.

In view of the foregoing, there exists a need for a low-cost non-labile preserving agent, particularly a carbohydrate preserving agent, that is effective in the protection of materials that are susceptible to degradation and that is compatible with such materials. There also is a need for a method of protecting such materials against degradation during isolation and storage.

THE INVENTION

The present invention is predicated on the surprising discovery that reduced malto-oligosaccharides have preserving properties.

In accordance with the invention, a composition that includes a material that is susceptible to degradation and a preserving agent that comprises one or more reduced malto-oligosaccharide species in an amount effective to inhibit the degradation of the material is provided. By "degradation" is contemplated a structural or chemical change in the material (such as chemical degradation or reaction with a carrier), and/or a loss of activity or function of the material (for instance, the loss of activity of an enzyme) or a change in conformation of a protein. The preserving agent of the present invention can include a single reduced malto-oligosaccharide species or plurality of such species. While the reduced malto-oligosaccharides used in conjunction with the present invention can be obtained by any suitable method, the malto-oligosaccharides are preferably prepared via reduction of readily available malto-oligosaccharide(s), e.g., as described in allowed U.S. patent application Ser. No. 09/366,065 (corresponding to WO 99/36442).

A variety of materials can be preserved with reduced malto-oligosaccharides in accordance with the invention. Such materials include, for example, compounds that react with a carbohydrate carbonyl substituent such as an aldehyde substituent or ketone, photochemically reactive materials, materials that react upon exposure to atmospheric oxygen, oxidants, reducing agents, polymerizable materials, catalysts, coloring agents, flavoring agents, proteins, mixtures thereof, and the like, and precursors thereof, biological materials (e.g., tissues, cells (e.g., yeasts and organelles) and biologically active compounds (including mixtures thereof and precursors thereof). The reduced malto-oligosaccharides also may be used to preserve extracts (natural or synthetic) containing such materials as well as mixtures of such materials and precursors thereof. The composition of the present invention can be in any suitable form (e.g., granules, dry powder, solution, gel, glass, or the like).

The present invention further provides a method of preserving a material. In accordance with the invention, the method includes contacting the material with a preserving effective amount of preserving agent that comprises one or more reduced malto-oligosaccharide species, as well as a method of storing a material that comprises storing the composition formed upon contacting the material with the preserving agent. The composition can be stored in any suitable form, for example, as a solid composition, gel, glass, or rubbery substance.

These and other advantages of the present invention, as well as additional inventive features, will be apparent from the description of the invention provided herein.

DESCRIPTION OF THE PREFERRED EMBODIMENTS

Figure 1:
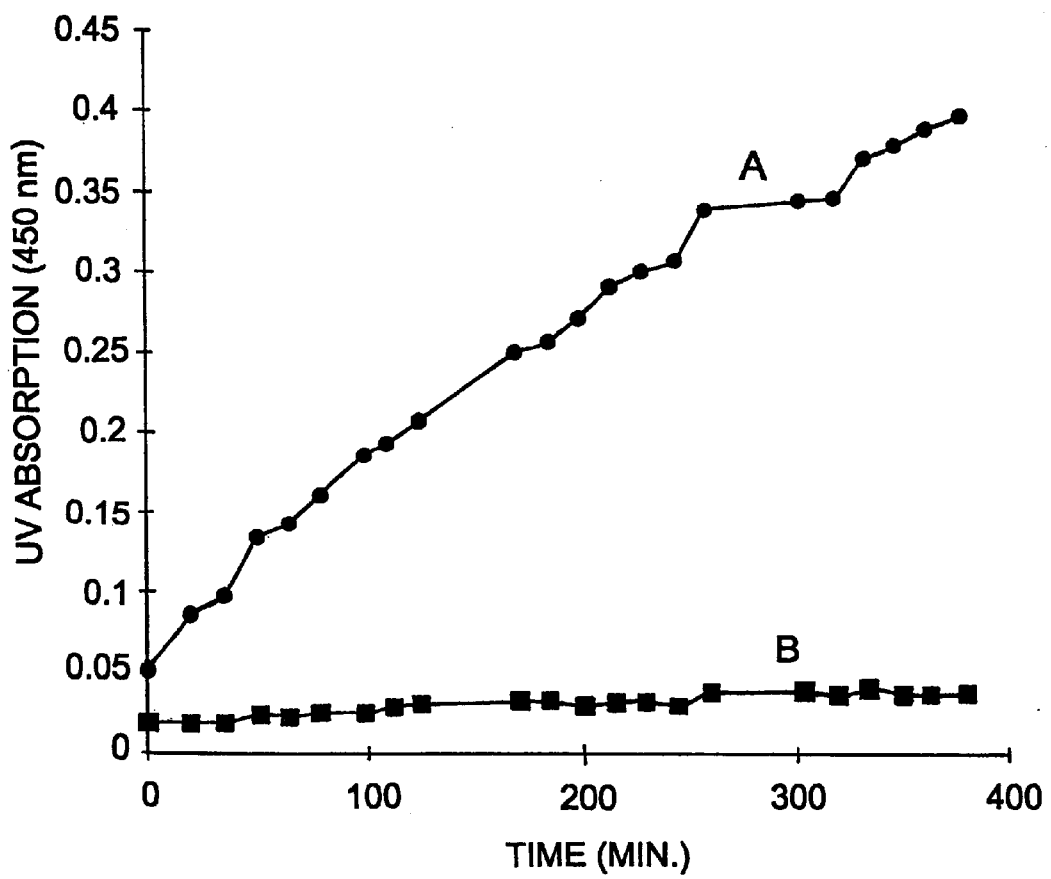
FIG. 1 is a graph depicting the compatibility of lysine with a known malto-oligosaccharide (curve A) relative to a reduced malto-oligosaccharide of the present invention (curve B).

Generally, the composition of the invention includes a material that is susceptible to degradation and a preserving agent present in an amount effective to preserve the material, the preserving agent comprising one or more reduced malto-oligosaccharide species. The terms "preserve" and "preserving" refer to the ability of a preserving agent to inhibit degradation of a material, such as structural change or loss of activity or function of the material, for example, by reducing the rate of degradation that would otherwise occur in the absence of the preserving agent. The useful shelf life of a material thus preserved can be extended for a period of time which may be days, hours, weeks, months, or years. In accordance with the invention, the material that is subject to degradation in the composition is capable of being preserved by a preserving agent comprising one or more reduced malto-oligosaccharide species. Preferably, the material used in accordance with the invention can be preserved more effectively with a preserving agent comprising one or more reduced malto-oligosaccharide species than with a preserving agent comprising the corresponding one or more unreduced malto-oligosaccharide species.

The preserving agent can include a single reduced malto-oligosaccharide species or a plurality of such species. While the reduced malto-oligosaccharide species can be obtained by any suitable method such as chemical reduction, they are preferably prepared via catalytic reduction (hydrogenation) of readily available malto-oligosaccharide mixtures, e.g., as described in U.S. patent application Ser. No. 09/366,065 (corresponding to WO 99/36442). Malto-oligosaccharide mixtures suitable for reduction to form reduced malto-oligosaccharides are sold by Grain Processing Corporation of Muscatine, Iowa under the MALTRIN® product designation, these including, for example, MALTRIN® M040, MALTRIN® M050, MALTRIN® M100, MALTRIN® M150, and MALTRIN® M180. It will be appreciated that naturally occurring malto-oligosaccharides typically contain a mixture of a plurality of malto-oligosaccharide species. As such, the reduced malto-oligosaccharide species obtained by reduction of such naturally occurring precursors likewise will contain a plurality of reduced malto-oligosaccharide species.

Oligosaccharides can be prepared by the controlled hydrolytic cleavage of starches. In the production of such oligosaccharides, the glycoside linkages of the starch molecules are partially hydrolyzed to yield at least one oligosaccharide species, and more typically, a mixture of oligosaccharide species. Each oligosaccharide species in the mixture may be characterized by its degree of polymerization (DP), which refers to the number of saccharide units in the molecule. Each oligosaccharide species also may be characterized by its dextrose equivalent (DE), which generally indicates the proportion of aldehyde, hemiacetal or ketone terminal groups in the molecule, and which is a measure of the reducing sugar content of the oligosaccharide, expressed as a percentage of the total dry substance. The DE value and DP profile for a given oligosaccharide mixture can vary substantially, depending, for example, upon the type of starch precursor used to obtain the mixture and the conditions employed for hydrolysis of the base starch.

When a reduced malto-oligosaccharide species is obtained by reduction of a malto-oligosaccharide precursor, it will be appreciated that the DP value of the reduced product may be different from the DP value of the precursor. The malto-oligosaccharide preferably is reduced under conditions such that when a single reduced malto-oligosaccharide species is obtained by reduction of a malto-oligosaccharide precursor, the DP value of the reduced malto-oligosaccharide species preferably is substantially preserved. Similarly, when a mixture of a plurality of reduced malto-oligosaccharide species is obtained by reduction of a mixture of a plurality of malto-oligosaccharide species, the DP profile for the product preferably is substantially retained, e.g., as described in U.S. patent application Ser. No. 09/366,065 (corresponding to WO 99/36442). Preferably, the reduced malto-oligosaccharide species used in accordance with the present invention has a DE of less than about 1.

The preserving agents used in accordance with the invention have been found to possess excellent heat and pH stability. Accordingly, the preserving agents used in accordance with the invention are believed to be particularly useful in applications or processes that involve heat, as well as acidic or basic conditions. Such preserving agents are also believed to be particularly useful in preserving acidic and basic materials that are subject to degradation, as described herein.

The reduced malto-oligosaccharide species used in conjunction with the invention can have any suitable DP value, preferably 2 or greater and typically greater than 2 (e.g., DP of 5 or greater). In a preferred embodiment, the preserving agent includes a mixture of a plurality of reduced malto-oligosaccharide species differing at least in DP value thus defining a DP profile for the mixture. When a mixture of a plurality of reduced malto-oligosaccharide species is utilized, it is preferred that at least one of the reduced malto-oligosaccharide species has a DP greater than 5, more preferably greater than about DP 8, and most preferably greater than about DP 10.

In a preferred embodiment, at least about 80% of the reduced malto-oligosaccharide species have a DP greater than 5. More preferably at least about 60% of the reduced malto-oligosaccharide species have a DP greater than 8. Still more preferably, at least about 60% of the reduced malto-oligosaccharide species have a DP greater than 10. Most preferably, at least about 80% of the reduced malto-oligosaccharide species have a DP greater than 10. In a particularly preferred embodiment, at least about 75% of the reduced malto-oligosaccharide species in the mixture have a DP greater than 5 and at least about 40% of the reduced malto-oligosaccharide species in the mixture have a DP greater than 10.

While the reduced malto-oligosaccharide species of the preserving agent of the present invention are comprised of sugar units having different glucose linkages (typically 1,4- and 1,6-linkages) it is preferred that the majority of glucose units in the reduced malto-oligosaccharide species are 1,4-linked. When a mixture of a plurality of reduced malto-oligosaccharide species is used in the preserving agent of the present invention, it is highly preferred that at least about 80% of the species in the mixture have a DP greater than 5.

The reduced malto-oligosaccharides used in accordance with the present invention include modified reduced malto-oligosaccharides. Examples of modified reduced malto-oligosaccharides can be found, for example, in PCT/US00/40687, describing derivatized reduced malto-oligosaccharides. Derivatized reduced malto-oligosaccharides can include, for example, reduced malto-oligosaccharides that incorporate one or more substituents or chemical modifications in one or more positions on one or more saccharide units. Such substituents can be introduced, for example, by hydroxyalkylation, oxidation, etherification, and esterification reactions. By way of example, one or more primary alcohol positions in one or more saccharide units can be oxidized to form one or more carboxylic acids. Etherification reactions can include, for example, ethoxylations, propoxylations and other alkylations, as well as reactions that can introduce a cationic charge by using reagents such as, for example, 3-chloro-2-hydryoxypropyl-trimethylamonium chloride, or the like. Esterification reactions can include, for example, acylation reactions in which an acyl group (e.g., having from about 2 to 20 carbon atoms) is introduced to one or more saccharide units. It is contemplated that enzymatically modified reduced malto-oligosaccharides may be used in conjunction with the invention, as well as reduced malto-oligosaccharides that have been otherwise modified.

Any material subject to preservation with a reduced malto-oligosaccharide can be combined with the reduced malto-oligosaccharides of the present invention to preserve the material. For convenience, such materials may be separately considered as falling into one of two classes, chemically reactive materials and bioactive materials although many materials are susceptible to multiple forms of degradation. It is contemplated that at least contain embodiments of the classes of materials described herein are capable of being preserved by a preserving agent that comprises one or more reduced malto-oligosaccharide species. There is no intention to limit the invention to the particular materials or classes of materials disclosed herein, but to the contrary reduced malto-oligosaccharides may be found useful in connection with the preservation of other materials. It is further contemplated that mixtures of materials may be preserved.

By way of example, chemically reactive materials can include compounds that react with a carbohydrate carbonyl substituent (e.g., an aldehyde or ketone substituent), such as amines and alkaline materials; photochemically reactive materials, such as certain dyes; materials that react upon exposure to atmospheric oxygen, such as amino acids, aldehydes, thiols and thiol-containing compounds; oxidants, such as certain hypochlorites, persulfates, peroxides; reducing agents, such as certain organic thiols or inorganic sulfur compounds; polymerizable materials, such as acrylates, amino acids that polymerize or dimerize, and polymer precursors; catalysts, such as palladium, platinum, ferrocenes, transition metal organometallic catalysts, chiral amines (e.g., brucine), hydride-containing compounds (e.g., sodium borohydride), and the like; coloring agents; flavoring agents; proteins; and the like, as well as mixtures of the foregoing, including, for example, protein supplements that can be used in the fortification of food or drink comestibles (e.g., a proteinated drink), and the like. Precursors of the foregoing, extracts containing one or more of the foregoing, and mixtures of the foregoing also may be preserved in accordance with the invention.

Suitable bioactive materials can include enzymes, enzyme cofactors, proteins, peptides, amino acids, nucleosides, nucleotides, nucleic acids, antioxidants, vitamins, nutritional supplements, steroids, analgesics, anesthetics, sedatives, muscle relaxants, anti-infectives, anti-inflammatories, antineoplastics, antiseptics, antihypertensives, antihypotensives, adrenergic blockers, adrenergic agonists, anorexics, antacids, antiallergics, antianginals, antiarrhythmics, anticholinergics, anticonvulsants, antidepressants, antiemetics, antihyperlipidemics, antipsychotics, antiparkinsonians, antispasmodics, antitussives, antiulceratives, anxiolytics, bronchodilators, respiratory stimulants, antiathsmatics, vasodilators, vasoprotectants, cardiotonics, chelating agents, choleretics, cholinergics, CNS stimulants, contraceptives, expectorants, hemostatics, immunomodulators, immunosuppressants, decongestants, and laxatives. Precursors of the foregoing, extracts containing one or more of the foregoing, and mixtures of the foregoing are also deemed suitable for preservation.

In one preferred embodiment, the bioactive material is an antioxidant or a precursor thereof. Antioxidants that can be used in accordance with the present invention include, for example, caffeic acid, rosmarinic acid, gallic acid, ferulic acid, coumaric acid, and the like. In another preferred embodiment, the bioactive material is a biological extract. Biological extracts that can be used in accordance with the present invention include, for example, tea extracts, grape seed extracts, soy extracts, corn extracts, and the like. In yet another preferred embodiment, the bioactive material is an enzyme. Enzymes that can be used in accordance with the present invention include, for example, proteases, lipases, lactases, xylanases, cellulases, phosphatases, glycosyl tranferases, nucleases, mixtures of such enzymes, and the like.

The composition of the present invention can be in any suitable form (e.g., granules, dry powder, solution, gel, glass, or the like). For example, the composition of the present invention includes solutions (e.g., aqueous solutions) of the material and one or more reduced malto-oligosaccharide species; the solution may comprise a solvent in which the material and the preserving agent are dissolved. In one embodiment, the composition of the present invention includes one or more reduced malto-oligosaccharide species at a concentration that is sufficiently high such that the osmolality-of the solution is sufficient to inhibit (i.e., prevent or slow) microbial growth in the solution. More generally, the reduced malto-oligosaccharide species may be present in any total amount relative to the amount of material being preserved that is effective to impact a preserving effect. Preferably, the reduced malto-oligosaccharide species is present in a weight ratio with regard to the material being preserved ranging from about 100:1 to 1:100, more preferably from about 10:1 to 1:10. It is contemplated that this ratio will vary widely depending on the material that is to be preserved. The amount of reduced malto-oligosaccharide needed for a particular material may readily be determined by empirical evaluation.

The composition of the present invention also may take the form of solid compositions, gels, glasses, and the like. In one embodiment, the composition of the present invention is a spray-dried powder that includes one or more materials that are susceptible to degradation and a powder comprising a preserving effective amount of one or more reduced malto-oligosaccharide species. Some of the reduced malto-oligosaccharides used in accordance with the present invention are particularly useful for spray drying and for preparing spray dried powders. Factors such as molecular weight and DP profile can contribute to the effectiveness of some reduced malto-oligosaccharides as substrates for spray drying. For example, reduced malto-oligosaccharides obtained by reducing MALTRIN® series malto-oligosaccharides, wherein the DP profile is substantially preserved in the reduced product, are particularly stable under spray drying conditions and are useful in producing spray dried compositions in accordance with the invention.

In another embodiment, the composition of the present invention is a solid prepared by depositing one or more materials on a powder that comprises a preserving effective amount of one or more reduced malto-oligosaccharide species. The material can be deposited on the powder using any suitable method, for example, using a fluid bed dryer. In yet another embodiment, the composition of the present invention is a glassy or rubbery substance that includes a material and a preserving effective amount of one or more reduced malto-oligosaccharide species. The glassy or rubbery substance may be prepared in accordance with the methods described in U.S. Pat. No. 5,098,893.

The present invention further provides a method of preserving a material that is susceptible to degradation. Generally, the method includes the steps of contacting the material with a preserving agent containing a preserving effective amount of one or more reduced malto-oligosaccharide species. For example, in one embodiment, the method of preserving a susceptible material in accordance with the present invention includes providing a solution containing the material and a preserving agent that comprises one or more reduced malto-oligosaccharide species, and drying the solution. The solvent can be aqueous, organic, or any suitable combination thereof, but is preferably aqueous. The composition thus produced is a dried composition that includes the material and the preserving agent, the reduced malto-oligosaccharide species being present in an amount effective to preserve the material. The solution may be dried to yield a dried composition. The drying or desiccation process can be carried out using any suitable technique, such as distillation (e.g., rotary-evaporation, heat distillation, steam distillation or the like), spray drying, fluid bed drying, and freeze-drying. When the material is-a bioactive material, the drying is preferably carried out by spray drying or freeze drying.

In another embodiment, the method of the present invention includes the step of depositing the one or more materials to be preserved onto a powder containing a reduced malto-oligosaccharide species to produce a composition that includes the susceptible material or materials, the reduced malto-oligosaccharide species being present in an amount effective to preserve the material deposited on the powder. The susceptible material or materials can be deposited on the powder using any suitable method, for example, using a fluid bed dryer.

In still another embodiment, the method of the present invention includes the step of preparing an aqueous solution of one or more materials to be preserved and a preserving agent that contains a preserving effective amount of one or more reduced malto-oligosaccharide species. In a preferred embodiment, the concentration of the reduced malto-oligosaccharide species in the solution is sufficiently high such that the osmolality of the solution is effective to inhibit (i.e., prevent or retard) microbial growth. In yet another embodiment, the method includes dissolving one or more susceptible materials in a solution containing one or more reduced malto-oligosaccharide species to form a glassy or rubbery composition.

The invention further provides a method of storing a susceptible material. Generally, the method includes the step of storing the composition formed in accordance with the foregoing techniques. When the composition is a liquid composition, it optionally may be dried before storing. The composition can be stored in any suitable form, for example, as a solid composition, gel, glass, or rubbery substance, as described herein, for a period of time that may be plural minutes, hours, days, weeks, months, or years, depending on the material and particular circumstances of storage.

The following examples further illustrate the present invention but, of course, should not be construed as in any way limiting its scope.

EXAMPLE 1

This example illustrates a method of preparing a reduced malto-oligosaccharide that can be used as a preserving agent in accordance with the present invention.

In 650 ml of deionized water was dissolved 567 g of MALTRIN® M100 maltodextrin (5.6% moisture, produced by Grain Processing Corporation, Muscatine, Iowa). Sodium borohydride, 28.5 ml (12% solution, 14M NaOH) was slowly added to the stirred mixture at ambient temperature. The initial pH of the solution was measured and found to be pH 11.8.

The mixture was stirred overnight (17.5 hrs.) and quenched by adjusting the pH with 7% HCl solution to a pH of 7.3. The sample was then frozen and freeze-dried to yield 573 g of product, the product including 2% moisture and 5.37% ash.

A 393 g sample of product was purified by passing the product through two series of alternating columns of DOWEX™ MONO 88 strong cationic exchange resin in the hydrogen form, and of DOWEXTM MONO 66 weak anionic exchange resin in the free base form. The DE of the resultant reduced malto-oligosaccharide was 0.8.

EXAMPLE 2

This example illustrates a catalytic method for preparing a reduced malto-oligosaccharide that can be used as a preserving agent in accordance with the present invention.

MALTRIN® M180 maltodextrin, 519 g (5.5% moisture, produced by Grain Processing Corporation, Muscatine, Iowa) was added to 881 ml water and stirred for approximately 30 minutes to obtain a clear solution. Raney® nickel GD3110 (Grace Davison), 18.4 g (3.7% dry solids basis catalyst/maltodextrin w/w) was added and the mixture was stirred for another 10 minutes. The entire mixture (ca. 35% solids by weight) was then transferred to a 2.0 L Parr 4522 M reactor. The unit was sealed and stirring was continued at 600 rpm. The Parr reactor was pressurized to 500 psi with hydrogen gas and heated to 120° C. After 4 hours at 120° C., the reaction was stopped by cooling and then depressurization. The reaction contents were filtered through Whatman® No. 1 filter paper to give a clear viscous solution. The sample was then purified by ion exchanged as described in Example 1. No detectable ash was found after ion exchange. The sample was freeze dried after ion exchange to yield a reduced malto-oligosaccharide mixture having a DE of 0.46 and an ash content of 0%.

EXAMPLE 3

This example illustrates the preparation of a composition in accordance with the present invention.

A solution of a reduced malto-oligosaccharide is prepared by dissolving a reduced malto-oligosaccharide in distilled water. Slight heating is applied (35° C.) to facilitate dissolution of the reduced malto-oligosaccharide. An air-oxidizable amine is dissolved in the aqueous solution and the resulting solution is spray dried using a Yamato® DL-41 spray dryer (inlet temperature: 300° C., outlet temperature: 80° C.), to produce a spray-dried powder.

EXAMPLE 4

This example illustrates the preparation of a composition in accordance with the present invention.

An aqueous solution of a reduced malto-oligosaccharide is prepared by dissolving a reduced malto-oligosaccharide (309 g, 97% solids by weight) in distilled water (1161 g). Slight heating is applied (35° C.) to facilitate dissolution of the reduced malto-oligosaccharide. A ferulic acid extract from corn (100 g) is dissolved in the aqueous solution and the resulting solution is spray dried using a Yamato® DL-41 spray dryer (inlet temperature: 300° C., outlet temperature: 80° C.), to produce a spray-dried powder. The resulting powder is a stabilized composition having anti-oxidant properties. The anti-oxidant properties of the ferulic acid extract are protected from loss of anti-oxidant activity and the ferulic acid is compatible with the reduced malto-oligosaccharide in the composition.

EXAMPLE 5

This example illustrates the preparation of a composition in accordance with the present invention.

A pH 6 buffered lysine solution was prepared by dissolving L-lysine (0.5 g) in phosphate buffer and adjusting the pH with hydrochloric acid. The buffered lysine solution thus produced had a final solids content of 10% by weight. An aqueous solution of a reduced malto-oligosaccharide was prepared by dissolving a reduced malto-oligosaccharide mixture in water to produce a solution having a final solids content of 50% by weight. The buffered lysine solution (2 mL) was dissolved in the aqueous reduced malto-oligosaccharide solution (hydrogenated MALTRIN® M180) (3 mL) to produce a solution. The final solution thus produced was a stabilized composition in which L-lysine was protected from degradation. Moreover, the L-lysine had excellent compatibility with the reduced malto-oligosaccharide in the stabilized composition.

EXAMPLE 6

This example illustrates the preserving effect of a reduced malto-oligosaccharide.

The sample prepared in accordance with Example 5 was warmed to 75° C. and the ultraviolet absorption (450 nm) of the solution was monitored over time. The ultraviolet absorption measured over time is shown below in Table 1 and is graphically depicted in FIG. 1 (curve B).

TABLE 1

| | UV absorption (450 nm) | |
|---|---|---|
| Time (min.) | Control (lysine only) | Sample (Lysine and Reduced Malto-oligosaccharide) |
| 0 | 0.044 | 0.019 |
| 20 | 0.043 | 0.020 |
| 35 | 0.044 | 0.020 |
| 50 | 0.046 | 0.027 |
| 65 | 0.047 | 0.025 |
| 80 | 0.048 | 0.028 |
| 100 | 0.050 | 0.028 |
| 110 | 0.050 | 0.031 |
| 125 | 0.051 | 0.032 |
| 170 | 0.055 | 0.034 |
| 185 | 0.057 | 0.033 |
| 200 | 0.057 | 0.031 |
| 215 | 0.059 | 0.036 |
| 230 | 0.059 | 0.034 |
| 245 | 0.058 | 0.033 |
| 260 | 0.061 | 0.041 |
| 305 | 0.061 | 0.041 |
| 320 | 0.063 | 0.039 |
| 335 | 0.063 | 0.044 |
| 350 | 0.063 | 0.039 |
| 365 | 0.064 | 0.039 |
| 380 | 0.065 | 0.040 |

The foregoing data illustrate that the reduced malto-oligosaccharide exhibited excellent compatibility with the L-lysine. The composition exhibited only a slight change in ultraviolet absorption over time as compared with the control, as indicated by the low level of ultraviolet adsorption and small slope for curve B of FIG. 1.

COMPARATIVE EXAMPLE 1

A sample of MALTRIN® M180 maltodextrin (the starting material of Example 2) was dissolved in water to produce a malto-oligosaccharide solution having a final solids content of 50% by weight. A buffered L-lysine solution prepared in Example 4 (2 ml) was added to the MALTRIN® M180 solution (3 ml) and this solution was heated and monitored for uv absorption in accordance with Example 6. The comparative sample used in this example was prepared as described in Example 5, except that the reduced malto-oligosaccharide was replaced by the corresponding unreduced malto-oligosaccharide. The change in ultraviolet absorption over time is shown below in Table 2 and is graphically depicted in FIG. 1 (curve A).

TABLE 2

| | UV absorption (450 nm) | |
|---|---|---|
| Time (min.) | Control (lysine only) | Comparative Sample (Lysine and Malto-oligosaccharide) |
| 0 | 0.044 | 0.050 |
| 20 | 0.043 | 0.087 |
| 35 | 0.044 | 0.098 |
| 50 | 0.046 | 0.135 |
| 65 | 0.047 | 0.144 |
| 80 | 0.048 | 0.161 |
| 100 | 0.050 | 0.187 |
| 110 | 0.050 | 0.193 |
| 125 | 0.051 | 0.208 |
| 170 | 0.055 | 0.251 |
| 185 | 0.057 | 0.257 |
| 200 | 0.057 | 0.272 |
| 215 | 0.059 | 0.292 |
| 230 | 0.059 | 0.301 |
| 245 | 0.058 | 0.308 |
| 260 | 0.061 | 0.341 |
| 305 | 0.061 | 0.345 |

TABLE 2-continued

| | UV absorption (450 nm) | |
|---|---|---|
| Time (min.) | Control (lysine only) | Comparative Sample (Lysine and Malto-oligosaccharide) |
| 320 | 0.063 | 0.347 |
| 335 | 0.063 | 0.371 |
| 350 | 0.063 | 0.379 |
| 365 | 0.064 | 0.390 |
| 380 | 0.065 | 0.399 |

The comparative sample exhibited a significant change in ultraviolet absorption over time, as indicated by the ultraviolet absorption of about 0.40 after 380 minutes. After 380 minutes, the ultraviolet absorption for the comparative sample was about ten times greater than the ultraviolet absorption for the sample of Example 5 (of the present invention). Moreover, in FIG. 1, curve A has a significantly higher slope relative to the slope of curve B. It is believed that the change in ultraviolet absorption is due at least in part to reactivity between the malto-oligosaccharide and the lysine.

EXAMPLE 7

This example illustrates the ability of reduced malto-oligosaccharides to protect a bioactive molecule under the stresses of spray drying.

An aqueous solution of a reduced malto-oligosaccharide (MALTRIN® M180) was prepared by dissolving a reduced malto-oligosaccharide (309 g, 97% solids by weight) in distilled water (1161 g). Slight heating was applied (35° C.) to facilitate dissolution of the reduced malto-oligosaccharide. A 30 g sample of Xylanase GC 140 (available from Genencor International, Inc., Rochester N.Y.) was added to the solution, and the mixture was stirred for about 2 hours at 25–35° C. The resulting solution was then spray dried using a Yamato® DL-41 spray dryer (inlet temperature: 300° C., outlet temperature: 80° C., pump feed rate: 20 ml/min.), to produce a spray-dried powder. The resulting spray-dried powder was analyzed for xylanase activity using a Megazyme® endo β-xylanase assay kit (Megazyme International Ireland Ltd., Wicklow, Ireland). The spray-dried powder had a residual activity of 40% relative to the enzyme/reduced malto-oligosaccharide solution prior to spraying.

COMPARATIVE EXAMPLE 2

This example illustrates the ability of a known malto-oligosaccharide to protect a bioactive molecule under the stresses of spray drying.

A comparative sample was prepared by dissolving of 323 g of unreduced MALTRIN® M100 maltodextrin (92.8% solids by weight), in 1147 g of distilled water. Slight heating was applied (35° C.) to facilitate dissolution of the maltodextrin. A 30 g sample of Xylanase GC 140 (Genencor International, Inc., Rochester N.Y.) was added to the solution and the mixture was stirred for about 2 hours at 25–35° C. The resulting solution was then spray dried using a Yamato® DL-41 spray dryer (inlet temperature: 300° C., outlet temperature: 80° C., pump feed rate: 20 ml/min.), to produce a spray-dried powder. The resulting spray-dried powder was analyzed for xylanase activity using a Megazyme® endo β-xylanase assay kit (Megazyme International Ireland Ltd., Wicklow, Ireland). The spray-dried powder had a residual activity of 12% relative to the enzyme/maltodextrin solution prior to spraying.

The foregoing data demonstrate that the reduced malto-oligosaccharide of the present invention significantly outperformed the corresponding malto-oligosaccharide in terms the ability to protect xylanase against loss of activity under the stresses of spray drying. When the xylanase was spray dried in the presence of MALTRIN® M100 maltodextrin, only 12% of the activity was retained. However, when the xylanase was spray dried in the presence of the reduced malto-oligosaccharide of the present invention, it retained more than three-fold greater enzymatic activity (40% as compared to 12%). Based on this data, the protective ability of the reduced malto-oligosaccharide of the present invention was more than three times greater than that of the corresponding malto-oligosaccharide.

EXAMPLE 8

This example illustrates the ability of reduced malto-oligosaccharides to protect a bioactive material under freeze drying conditions. The bioactive material used in this example was lactase enzyme.

The enzyme activity was determined in accordance with Mazzobre et al., Biopolymer Science: *Food and Non Food Applications*, Montpellier (France) Sep. 28–30, 1998 Ed. INRA, Paris, 1999 (Les Colloques, no 91). The procedure is based on measuring the amount of glucose released from a buffered lactose solution. The measurement was done using a YSI 2700 glucose analyzer.

For comparison, a mixture containing lactase and a malto-oligosaccharide was prepared, as follows. A 20% aqueous solution of MALTRIN® M180 (M180) was prepared by dissolving 85.5 g (6.4% moisture) of M180 in 313.5 g of deionized water. Enzeco® Fungal Lactase Concentrate, 1.0 g was added to the slurry and stirred for one hour. A 20.0 ml aliquot of the mixture was removed as a control (sample 8A). The remaining sample was poured into two separate freeze drying pans and each was freeze dried according to the temperature profile in Table 3. The temperature profile shown in column 8B of Table 3 represents the temperature profile for only one of the two samples in the freeze drying pans. The freeze dryer was a Virtis Genesis 25XL unit. Final vacuum of the system was 11.8 mtorr. After freeze drying, the material was removed from the pans and evaluated for enzyme activity. The enzyme activity data is shown in Table 4. The enzyme activity in column 8B of Table 4 represents an average of the enzyme activities for each of the two samples in the freeze drying pans.

A mixture containing lactase and a reduced malto-oligosaccharide was freeze dried as follows. A 20% aqueous solution of reduced malto-oligosaccharide with a carbohydrate profile that matches MALTRIN® M180 (H-M180) was prepared by dissolving 83.4 g (4.1% moisture) of the reduced malto-oligosaccharide in 315.6 g of deionized water. Enzeco® Fungal Lactase Concentrate (1.0 g) was added to the slurry and stirred for one hour. A 20.0 ml aliquot of the mixture was removed as a control (sample 8C). The remaining sample was poured into two separate freeze drying pans and freeze dried according to the temperature profile in Table 3 (samples 8D-1 and 8D-2). The freeze dryer was a Virtis Genesis 25XL unit. Final vacuum of the system was 11.8 mtorr. After freeze drying, the material was removed from the pans and evaluated for enzyme activity as described in the previous example. The enzyme activities of samples 8D-1 and 8D-2 were averaged (sample 8D), and the data is shown in Table 4.

For comparison, a mixture containing lactase and trehalose was freeze dried, as follows. A 20% aqueous solution of trehalose was prepared by dissolving 88.9 g (9.1% moisture) of trehalose in 311.0 g of deionized water. Enzeco® Fungal Lactase Concentrate, 1.0 g was added to the slurry and stirred for-one hour. A 20.0 ml aliquot of the mixture was removed as a control (sample 8E). The remaining sample was poured into two separate freeze drying pans and each was freeze dried according to the temperature profile in Table 3. The temperature profile shown in column 8F of Table 3 represents the temperature profile of only one of the two samples in the freeze drying pans. The freeze dryer was a Virtis Genesis 25XL unit. Final vacuum of the system was 11.8 mtorr. After freeze drying, the material was removed from the pans and evaluated for enzyme activity as described in the previous example. The enzyme activity data is shown in Table 4. The enzyme activity in column 8F of Table 4 represents an average of the enzyme activities for each of the two samples in the freeze drying pans.

The enzymatic activities shown in Table 4 are expressed as the percentage of glucose liberated in the enzyme assay as measured by the amount of glucose liberated divided by the maximum amount of glucose that can be theoretically liberated.

TABLE 3

| Time | Sample Temperature | | | | Vacuum |
| --- | --- | --- | --- | --- | --- |
| | 8B | 8D-1 | 8D-2 | 8F | |
| 0 min. | 21.4 | 20.7 | 21.1 | 20.2 | 1 atm |
| 10 | 18.0 | 18.4 | 19.0 | 18.4 | 1 atm |
| 30 | 7.4 | 8.1 | 9.2 | 8.5 | 1 atm |
| 55 | −1.2 | −1.1 | −0.8 | −1.9 | 1 atm |
| 85 | −14.6 | −12.0 | −7.6 | −11.4 | 1 atm |
| 120 | −30.9 | −30.2 | −29.9 | −30.2 | 1 atm |
| 160 | −43.3 | −42.2 | −43.4 | −42.8 | 1 atm |
| 200 | −54.2 | −52.7 | −54.7 | −53.7 | 1 atm |
| Freeze rate | −0.378° C./min | −0.367° C./min | −0.379° C./min | −0.370° C./min | |
| 230 | −51.1 | −48.2 | −52.2 | −50.7 | 1 atm |
| 255 | −45.1 | −41.8 | −47.2 | −44.4 | 1020 mtorr |
| 420 | −17.1 | −19.4 | −19.6 | −17.7 | 73.4 |
| 23 hours | 29.0 | 29.1 | 29.6 | 29.1 | 11.8 | in the presence of an unreduced malto-oligosaccharide (8A) or trehalose (8F).

EXAMPLE 9

This example illustrates the ability of reduced malto-oligosaccharides to protect a bioactive material under the stresses of freeze drying.

Yeast viability was determined by cell counting after plating on yeast extract, malt extract (YM) agar in accordance with the method described in FDA Bacteriological Analytical Manual, $6^{th}$ Ed., Ch. 4, pp. 401–402 (1984). Yeast viability is expressed as the number of cells per gram of dry solids (gm.ds). The percent yeast survival was determined by dividing the yeast viability of the freeze dried sample by the yeast viability of the control sample.

For comparison, a mixture of yeast cells and a malto-oligosaccharide was freeze dried, as follows. A 20% aqueous solution of MALTRIN® M180 (M180) was prepared by dissolving 85.5 g (6.4% moisture) of M180 in 304.5 g of deionized water. A suspension of yeast cells was prepared by dissolving 5.78 g of Fleischmann's baker's yeast in 94.3 g of sterile phosphate buffer. The yeast suspension was stirred for 30 minutes to obtain a relatively homogenous yeast mixture. A 10.0 ml aliquot of the yeast suspension was pipetted into the 20% aqueous M180 solution. A control sample was removed to determine yeast viability by plating on YM agar (sample 9A). The remaining sample was poured into two separate freeze drying pans and each was freeze dried according to the temperature profile in Table 5. The temperature profile shown in Table 5, column 9B, represents the temperature profile of only one of the two samples in the freeze drying pans. The freeze dryer was a Virtis Genesis 25XL unit. The final vacuum of the system was 9.3 mtorr. After freeze drying, sample 9B was removed from the pans and analyzed for yeast viability. The yeast viability data is shown in Table 6. The yeast viability data for 9B in Table 6 represents an average of the yeast viabilities for each of the two samples in the freeze drying pans.

A mixture of yeast cells and a reduced malto-oligosaccharide was freeze dried, as follows. A 20% aqueous solution of reduced malto-oligosaccharide with a carbohydrate profile that matches MALTRIN® M180 was prepared by dissolving 83.4 g (4.1% moisture) of reduced malto-oligosaccharide in 306.6 g of deionized water. A suspension of yeast cells was prepared by dissolving 5.78 g of Fleischmann's baker's yeast in 94.3 g of sterile phosphate buffer.

TABLE 4

| Time (h) | Control (M180) | | | Invention | | | Trehalose | | |
| --- | --- | --- | --- | --- | --- | --- | --- | --- | --- |
| | 8A | 8B | % activity* | 8C | 8D | % activity* | 8E | 8F | % activity* |
| 0 | 0 | 0 | 0 | 0 | 0 | 0 | 0 | 0 | 0 |
| 0.05 | 11.1 | 7.3 | 65.8 | 8.9 | 6.45 | 72.5 | 9.6 | 6.95 | 72.4 |
| 0.5 | 40.4 | 38.5 | 95.3 | 41.1 | 41.3 | 100.5 | 43.9 | 39.5 | 90.0 |
| 1 | 63 | 52.05 | 82.6 | 55.1 | 53.9 | 97.8 | 58.7 | 53.25 | 90.7 |
| 2 | 69.8 | 63.65 | 91.2 | 75.5 | 66.35 | 87.9 | 72 | 67.1 | 93.2 |
| Avg. | | | 83.7 | | | 89.7 | | | 86.6 |

*% activity was obtained by dividing enzyme activity of the freeze dried sample by the enzyme activity of the control sample (not freeze dried).

The data in Table 3 indicates that the lactase enzyme was frozen at similar rates of about −0.37° C./minute (from t=0 minutes to t=200 minutes). The data in Table 4 shows that the lactase enzyme activity when freeze dried in the presence of a reduced malto-oligosaccharide (8D) was comparable to or better than the enzyme activity when freeze dried The yeast suspension was stirred for 30 minutes to obtain a relatively homogenous yeast mixture. A 10.0 ml aliquot of the yeast suspension was pipetted into the 20% aqueous reduced malto-oligosaccharide solution. A control sample was removed to determine yeast viability by plating on YM agar (sample 9C). The remaining sample was poured into two separate freeze drying pans and freeze dried according to the temperature profile in Table 5 (samples 9D-1 and 9D-2). The freeze dryer was a Virtis Genesis 25XL unit. The final vacuum of the system was 9.3 mtorr. After freeze drying, samples 9D-1 and 9D-2 were removed from the pans and analyzed for yeast viability. The yeast viabilities of samples 9D-1 and 9D-2 were averaged (sample 9D). The yeast viability data is shown in Table 6.

For comparison, a mixture of yeast cells and trehalose was freeze dried, as follows. A 20% aqueous solution of trehalose was prepared by dissolving 88.0 g (9.1% moisture) of trehalose in 302.0 g of deionized water. A suspension of yeast cells was prepared by dissolving 5.78 g of Fleischmann's baker's yeast in 94.3 g of sterile phosphate buffer. The yeast suspension was stirred for 30 minutes to obtain a relatively homogenous yeast mixture. A 10.0 ml aliquot of the yeast suspension was pipetted into the 20% aqueous trehalose solution. A control sample was removed to determine yeast viability by plating on YM agar (sample 9E). The remaining sample was poured into two separate freeze drying pans and each was freeze dried according to the temperature profile in Table 5. The temperature profile shown in column 9F of Table 5 represents the temperature profile for only one of the two samples in the freeze drying pans. The freeze dryer was a Virtis Genesis 25XL unit. Final vacuum of the system was 9.3 mtorr. After freeze drying, sample 9F was removed from the pans and analyzed for yeast viability. The yeast viability data is shown in Table 6. The yeast viability data for 9F in Table 6 represents an average of the yeast viabilities for each of the two samples in the freeze drying pans.

TABLE 5

|      | Sample Temperature | | | | |
| Time | 9B | 9D-1 | 9D-2 | 9F | Vacuum |
| --- | --- | --- | --- | --- | --- |
| 5 min. | 24.8 | 25.7 | 25.2 | 24.8 | 1 atm |
| 20 | 19.1 | 20.0 | 19.3 | 19.5 | 1 atm |
| 40 | 6.4 | 8.1 | 6.5 | 7.7 | 1 atm |
| 75 | −0.9 | −1.0 | −0.8 | −2.6 | 1 atm |
| 90 | −10.3 | −3.8 | −8.8 | −5.0 | 1 atm |
| 140 | −31.1 | −29.6 | −32.0 | −30.7 | 1 atm |
| 210 | −49.8 | −47.9 | −51.4 | −50.5 | 1 atm |
| 245 | −46.9 | −44.2 | −47.7 | −46.4 | 840 mtorr |
| 280 | −44.5 | −42.8 | −44.8 | −44.0 | 191 |
| 320 | −34.4 | −35.1 | −34.5 | −33.7 | 57.7 |
| 445 | −17.7 | −19.4 | −17.2 | −24.3 | 77.6 |
| 22 hrs | 28.9 | 29.1 | 29.4 | 29.4 | 9.3 |

TABLE 6

| Sample | Yeast Viability (gm.ds) | % Yeast Survival |
| --- | --- | --- |
| 9A | $3.30 \times 10^7$ | 66.0 (M180) |
| 9B | $2.18 \times 10^7$ | |
| 9C | $2.74 \times 10^7$ | 78.8 (invention) |
| 9D | $2.16 \times 10^7$ | |
| 9E | $3.64 \times 10^7$ | 58.0 (trehalase) |
| 9F | $2.11 \times 10^7$ | |

The data in Table 5 indicates that the yeast cells were frozen at similar rates of about −0.35° C./minute (from t=5 minutes to t=210 minutes). The data in Table 6 shows that the yeast survival was significantly better when freeze dried in the presence of a reduced malto-oligosaccharide (9D) than when freeze dried in the presence of a malto-oligosaccharide (9B) or trehalose (9F).

The reduced malto-oligosaccharides of the present invention have excellent compatibility with many chemically reactive materials and are effective in preserving such materials. Moreover, the reduced malto-oligosaccharides of the present invention are readily available and are inexpensive as compared to other carbohydrates having good preserving properties such as, for example, trehalose. In addition, the molecular weight, water binding properties, viscosity, osmolality, and other functional properties of reduced malto-oligosaccharides render the reduced malto-oligosaccharides particularly suitable for use as preserving agents in many applications.

All of the references cited herein, including patents, patent applications, and publications, are hereby incorporated in their entireties by reference.

While this invention has been described with an emphasis upon preferred embodiments, it will be apparent to those of ordinary skill in the art that variations of the preferred embodiments may be used and that it is intended that the invention may be practiced otherwise than as specifically described herein. Accordingly, this invention includes all modifications and equivalents encompassed within the spirit and scope of the invention as defined by the following claims.

What is claimed is:

1. A method of preserving a material that is susceptible to degradation, the method comprising contacting said material with an amount of a preserving agent effective to inhibit the degradation of said material, said preserving agent comprising a mixture of a plurality of reduced malto-oligosaccharide species, said mixture having a dextrose equivalent (DE) of essentially zero, said mixture having been prepared from a mixture of reduced malto-oligosaccharide species each having a non zero DE resulting from the presence of a reducing end group on said reduced malto-oligosaccharide species, said plurality of reduced malto-oligosaccharide species differing at least in degree of polymerization (DP) value thus defining a DP profile for said mixture, at least about 40% of said reduced malto-oligosaccharides in said mixture having a DP value greater than 10, said plurality of reduced malto-oligosaccharides comprising a reduced malto-dextrin, said mixture having been prepared by:

providing said reduced malto-oligosaccharide mixture, and catalytically hydrogenating said mixture under hydrogenation conditions suitable to substantially preserve the DP profile of said mixture.

2. A method according to claim 1, comprising the steps of:

providing a solution containing said material and said preserving agent, and drying said solution to produce a dried composition comprising said material and said preserving agent, said preserving agent being present in said dried composition in an amount effective to inhibit the degradation of said material.

3. The method of claim 2, wherein said solution is spray dried.

4. The method according to claim 1, comprising the steps of:

providing a solution containing said material, providing one or more reduced malto-oligosaccharide species in powdered form, and depositing said material on said powder to form a powdered mixture, said preserving agent being present in said powdered mixture an amount effective to inhibit the degradation of said material.

5. The method according to claim 1, further comprising the step of storing said material after said material has been contacted with said preserving agent.

6. The method according to claim 1, the method including the step of drying said material.

7. A method of preserving a chemically reactive material that is susceptible to degradation or loss of activity or function, said method comprising preparing a solution comprising a material that is susceptible to degradation and a preserving agent, said preserving agent comprising a mixture of a plurality of reduced malto-oligosaccharide species, said mixture having a dextrose equivalent (DE) of essentially zero, said mixture having been prepared from a mixture of reduced malto-oligosaccharide species each having a non zero DP resulting from the presence of a reducing end group on said reduced malto-oligosaccharide species, said plurality of reduced malto-oligosaccharide species differing at least in degree of polymerization (DP) value thus defining a DP profile for said mixture, at least about 40% of said reduced malto-oligossaccharides in said mixture having a DP value greater than 10, said plurality of reduced malto-oligosaccharides comprising a reduced malto-dextrin, said mixture having been prepared by:

providing said reduced malto-oligosaccharide mixture, and catalytically hydrogenating said mixture under hydrogenation conditions suitable to substantially preserve the DP profile of said mixture, wherein the concentration of said plurality of reduced malto-oligosaccharide species is effective to preserve said material.

8. The method of claim 7, wherein said solution comprises a solvent, and said material and said preserving agent are dissolved in said solvent.

* * * * *